Dec. 5, 1972 W. H. JESSEL, JR., ET AL Plant Pat. 3,262
CHRYSANTHEMUM PLANT
Filed Oct. 14, 1970
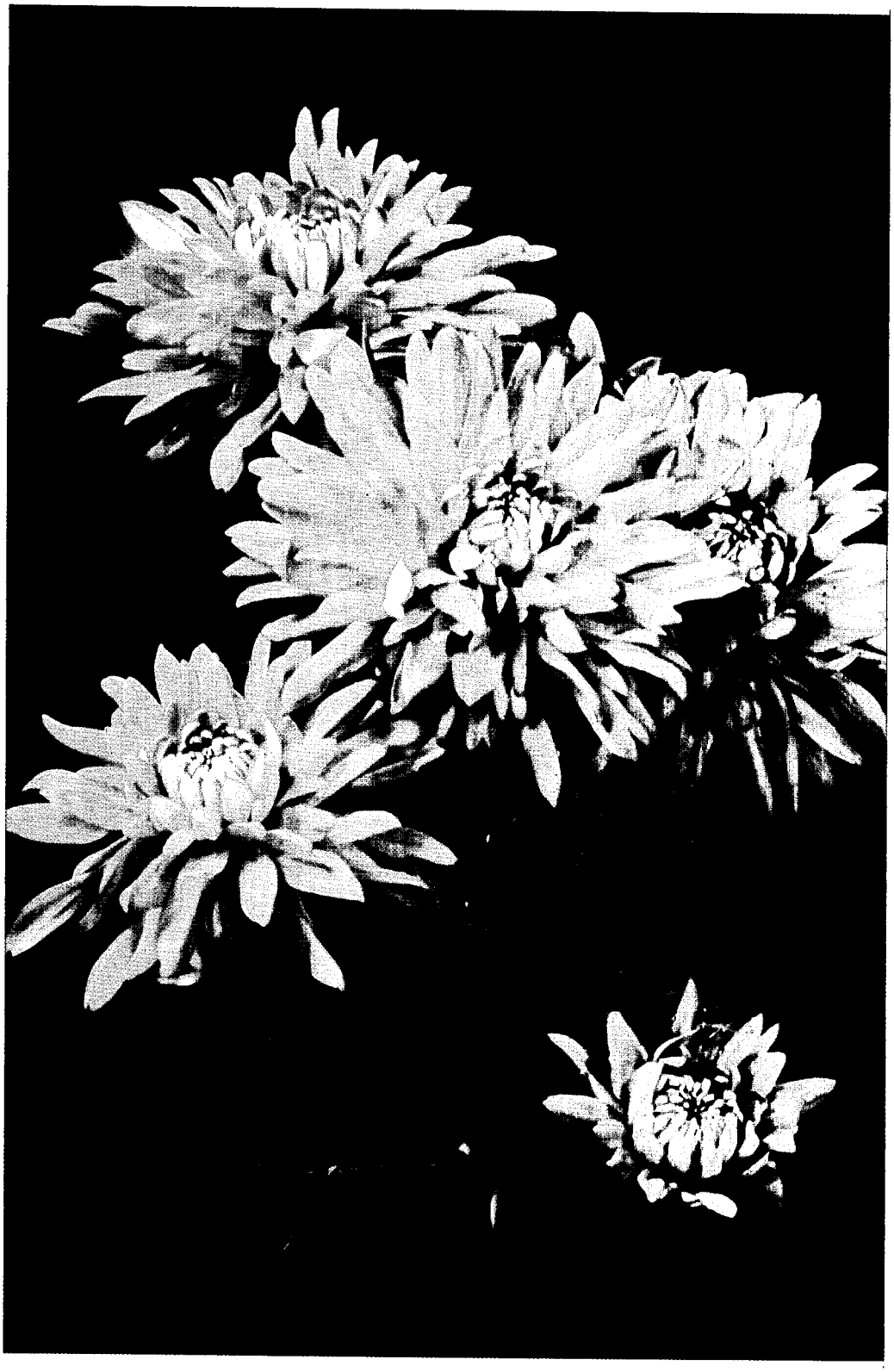

United States Patent Office

Plant Pat. 3,262
Patented Dec. 5, 1972

3,262

CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 14, 1970, Ser. No. 80,825
Int. Cl. A01h *5/00*
U.S. Cl. Plt.—82 1 Claim

The present invention comprises a new and distinct cultivar of chrysanthemum plant which is a sport of the cultivar known in the United States as Stingray, an unpatented but commercially well-known variety of Yoder Brothers, Inc., Barberton, Ohio, the assignee of the present invention.

The new cultivar is similar in many respects to Stingray, having the same characteristics as Stingray of:

(1) Flower size.
(2) Foliage size.
(3) Foliage shape.
(4) Foliage color.

The new cultivar is distinguished from Stingray by the following characteristics:

(1) Four inches to eight inches more vigor.
(2) Three to four days later response.
(3) Somewhat more longitudinal petal roll giving a more pointed appearance.
(4) More intense red color.

The new cultivar was selected from a flowering block of the parent cultivar in Barberton, Ohio, and when asexually reproduced by cuttings has been found to retain its distinctive characteristics through successive propagations.

The new cultivar when grown in the vicinity of Barberton, Ohio, has a response period of approximately 10 to 11 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern, mid-western United States and California is from January through December. In Florida, from December through April. In the southern United States from November through April.

The accompanying drawing shows the unique characteristics of the new cultivar, the color being as nearly true as possible with color illustrations of this type.

In the following description, color references are to the Munsell Color Book, 1963 edition, and represent the closest available color keys. Comparisons have been made, where characteristics differ, with the parent cultivar Stingray.

Botanical Classification: Chrysanthemum morifolium.

Bloom:

*Size.*—3¼".
*Fully expanded.*—3¾".
*Borne.*—Clusters on elongated pedicels.
*Stems.*—Wiry.
*Form.*—Decorative.
*Permanence.*—7–10 days.

| | Red Stingray | Stingray |
|---|---|---|
| Color: | | |
| Center of flower | Light bronze, 2.5Y6/4 to yellow bronze, 2.5Y7/8. | Yellow bronze, 2.5Y7/8 to light yellow bronze, 2.5Y7/6. |
| Base of petals | Maroon, 10R2/6 to red bronze, 10R3/10. | Red bronze, 10R3/10 to orange bronze, 1.25YR5/12. |
| Inside of petals | Orange bronze, 1.25YR5/12 to close to maroon, 10R2/6. | Orange bronze, 1.25YR5/12 to orange bronze, 2.5YR5/10. |
| Reverse of petals | Light bronze, 2.5Y6/8 to yellow bronze, 10YR6/10. | Yellow bronze, 10YR6/10 to yellow bronze, 2.5Y7/8. |
| Tonality from a distance. | Dark red, approximately 7.5R3/10. | Red bronze. |
| Discoloration | Orange bronze, 1.25YR5/12. | Orange bronze, 2.5YR5/10. |
| Petals: | | |
| Texture | Smooth | Smooth. |
| Appearance and form. | Open at base, center ridged, longitudinal roll, tapering to a sharp point. | Open at base, center ridged, tapering to a sharp point. |
| Arrangement | Composite, whorled on a single receptacle. | Composite, whorled on a single receptacle |
| Persistence | Resist shatter | Resist shatter. |
| Fragrance | Typical chrysanthemum | Typical chrysanthemum. |

Reproductive organs:

*Stamen, anthers.*—None to 25.
*Pollen.*—None to scant.
*Arrangement.*—Clustered in center of flower, if present.
*Styles.*—Present both ray and disc florets.
*Length.*—Short.
*Ovaries.*—At the base of petal attached to receptacle.

Plant:

*Form.*—Herbaceous.
*Growth.*—Upright.
*Height.*—Depending on culture—50"–54" (by way of contrast, Stingray is approximately 46").
*Spread.*—None when grown single stem to moderate when grown pinched.

Foliage:

*Top side.*—Green, 7.5GY3/4.
*Size.*—7" long; 4¾" wide.
*Quantity.*—Numerous.
*Shape.*—Spatulate lobed.
*Texture.*—Smooth.
*Ribs and veins.*—Very prominent.
*Edge.*—Deeply indented.
*Serration.*—Slight.
*Underside.*—Light green, 7.5GY5/4.
*Stipules.*—Prominent.

We claim:

1. A new and distinct cultivar of chrysanthemum characterized particularly to uniqueness when compared to the parent cultivar Stingray by its 4"–8" more vigor, its 3–4 days later response, a longitudinal petal roll giving a more pointed petal appearance, and a more intense red color.

No references cited.

ROBERT E. BAGWILL, Primary Examiner

Dedication

PP. 3,262.—*Walter H. Jessel, Jr.*, Doylestown, and *William E. Duffett*, Akron, Ohio. CHRYSANTHEMUM PLANT. Patent dated Dec. 5, 1972. Dedication filed Feb. 6, 1975, by the assignee, *Yoder Brothers, Inc.* Hereby dedicates to the Public the entire remaining term of said patent. [*Official Gazette July 1, 1975.*]